US006646186B1

(12) United States Patent
Stine et al.

(10) Patent No.: US 6,646,186 B1
(45) Date of Patent: Nov. 11, 2003

(54) HYBRID SOYBEANS AND METHODS OF PRODUCTION

(75) Inventors: Harry H. Stine, Adel, IA (US); William H. Eby, Adel, IA (US)

(73) Assignee: Stine Seed Farm Inc., Adel, IA (US)

(*) Notice: Subject to any disclaimer, the term of this patent is extended or adjusted under 35 U.S.C. 154(b) by 128 days.

(21) Appl. No.: 09/626,140

(22) Filed: Jul. 26, 2000

(51) Int. Cl.$^7$ .................................................. A01H 5/00
(52) U.S. Cl. ...................................................... 800/312
(58) Field of Search .............................. 800/260, 274, 800/278, 300, 312

(56) References Cited

U.S. PATENT DOCUMENTS

| | | |
|---|---|---|
| 3,903,645 A | 9/1975 | Bradner |
| 4,545,146 A | 10/1985 | Davis |
| 4,648,204 A | 3/1987 | Davis |
| 4,658,084 A | 4/1987 | Beversdorf et al. |
| 4,658,085 A | 4/1987 | Beversdorf et al. |
| 4,763,441 A | 8/1988 | Davis |
| 5,084,082 A | 1/1992 | Sebastian |
| 5,569,834 A | 10/1996 | Hinchee et al. |
| 5,824,877 A | 10/1998 | Hinchee et al. |
| 5,917,132 A | 6/1999 | Eby |
| 5,920,002 A | 7/1999 | Soper et al. |
| 5,952,548 A | 9/1999 | Jin et al. |
| 5,955,648 A | 9/1999 | Foster et al. |
| 6,066,779 A * | 5/2000 | Yan .............................. 800/274 |
| 6,077,991 A | 6/2000 | Poovaiah et al. |

FOREIGN PATENT DOCUMENTS

WO          WO 99/46396 A2        9/1999

OTHER PUBLICATIONS

Graybosch, Robert A., et al., "Male Sterility in Soybean—An Overview," *Amer. J. Bot.*, 1988, 75(1):144–156, USA.

Nelson, R.L., et al., "Production and Performance of Hybrid Soybeans," *Crop Science*, 1984, 24(3):549–553, USA.

* cited by examiner

*Primary Examiner*—Elizabeth F. McElwain
(74) *Attorney, Agent, or Firm*—Jondle & Associates PC

(57) ABSTRACT

An efficient method of producing hybrid $F_1$ soybean seeds is provided. A male sterile female parent line having a male sterile gene linked to a herbicide resistance gene is crossed with another male fertile soybean variety to produce hybrid soybean seeds.

29 Claims, No Drawings

HYBRID SOYBEANS AND METHODS OF PRODUCTION

BACKGROUND OF THE INVENTION

The present invention relates to a soybean (*Glycine max.*) seed, a soybean plant, a soybean variety, a soybean hybrid and methods for producing hybrid soybean seed and plants.

Soybeans (i.e., seeds of *Glycine max* plants) are recognized to be an important crop in many parts of the world. For instance, approximately 65 to 75 million acres of soybeans are planted annually in the United States. Various approaches to the production of hybrid soybeans are disclosed in the U.S. Pat. Nos. 3,903,645; 4,077,157; 4,545,146; 4,658,084; 4,648,204 and 4,763,441 which are herein incorporated by reference. Also, technical articles which discuss the existence of some degree of sterility in soybeans and the formation of hybrid soybean seeds are identified in U.S. Pat. No. 4,545,146.

For many crop species, it is well known that when different plant lines are cross-pollinated one can achieve in the offspring a highly desirable heterosis or hybrid vigor which advantageously provides increased yields of the desired crop.

Male sterility is a condition in plants in which male gametophytic function is prevented, but the potential for female reproduction remains. Based on inheritance patterns, there are two general types of male sterility: 1) genic or nuclear male sterility (gms) and 2) cytoplasmic male sterility (cms). Male-sterile mutations provide source material for studies in plant breeding, genetics, reproductive biology, and molecular biology.

Male sterility has been used in soybean breeding studies (Brim, C. A. et al., *Application of genetic male sterility to recurrent selection schemes in soybeans,* Crop Sci 13:528–530, 1973; Lewers, K. S., et al., *Hybrid soybean seed production: comparison of three methods,* Crop Sci 36:1560–1567, 1996), but so far male sterility has not been used for commercial production of a hybrid seed because large quantities of hybrid soybean seed cannot be produced at the present time. During the past two decades, six genic male sterile mutations (ms1, ms2, ms3, ms4, ms5 and ms6) have been reported in soybean (Palmer, R. G., et al., *Male sterility in soybean and maize: developmental comparisons,* Nucleus (Calcutta) 35:1–18, 1992). All of these are nuclear mutations inherited as monogenic recessive traits. Cytoplasmic male sterility has not been confirmed in soybean.

Genic male-sterile mutants have been proposed for many crop species breeding programs (Horner, H. T., et al., *Mechanisms of genic male sterility,* Crop Sci 35:1527–1535, 1995). Controlled production of hybrid seed is necessary for breeding programs and genetic studies. The most feasible methods should utilize close genetic linkage between a male-sterility locus and a seedling marker locus. In soybean, use of the close genetic linkage (Skorupska, H., et al., *Genetics and cytology of the ms6 male-sterile soybean,* J Hered. 80:403–410, 1989) between a male-sterility locus and a seedling marker locus (W1) is known as the co-segregation method to produce $F_1$ seeds (Lewers, K. S., et al. supra). The identification of additional soybean genic male steriles linked to a seedling marker locus would reduce the genetic vulnerability of soybean production of a single genic male sterile.

G. Marrewijk, *Cytoplasmic male sterility in petunia I. Restoration of fertility with special reference to the influence of environment,* Euphytica 18:1–20 (1969), reported that the phenotypic effect of partial male-sterility systems was subject to environmental modifications. Temperature has more influence than any other environmental factor: however, water stress, photoperiod, nutrients supplied, and hormone applications also influence male sterile phenotypes (Heslop-Harrison, J., *The experimental modification of sex expression in flowering plants,* Biol Rev 32:38–90, 1957; Edwardson, J. R., *Cytoplasmic male sterility,* Bot Rev 36:341–420, 1970). In soybean, the msp mutant is affected by temperature (Stelly, D. M., et al., *A partially male-sterile mutant line of soybeans Glycine max (L.) Merr.: characterization of msp phenotype variation,* Euphytica 29:539–546, 1980; and Carlson, D. R., et al., *Effect of temperature on the expression of male sterility in partially male-sterile soybean,* Crop Sci 25:646–648, 1985).

The male-sterile soybean mutants ms2 and ms3 result in a degeneration of tetrads because release of microspores from their encasing callose walls is prevented, a phenomenon also described in other, non-legume, species. For example, the failure of callose to break down at the proper time in cms petunia anthers resulted in sterility (Frankel, R. et al.,*Timing of callase activity and cytoplasmic male sterility in petunia,* Biochem Genet 3:451–455, 1969). The retention of callose seemingly blocks developmental metabolic processes (physical constraints are imposed by the callose wall) and intercellular communication between male cells and locular fluids and between male cells and surrounding tissues.

Examples of widely used herbicides are chlorimuron and thifensulfuron, which belong to the sulfonylurea class. They inhibit the plant enzyme acetolactate synthase (also called ALS), and soybeans which are resistant to these herbicides are referred to as STS (also called sulfonylurea tolerant) soybeans. These herbicides are the active ingredients in Classic™ and Pinnacle™, respectively, and are registered for control of broadleaf weeds in soybeans in Weed Science Society of America, Herbicide Handbook, 7th edition (1994). While chlorimuron and thifensulfuron are registered for use in non-STS soybeans, they can cause significant crop injury, especially if applied post-emergence in Fielding and Stoller, Weed Technol. 4:264–271 (1990); Fielding and Stoller, Weed Sci. 38:172–178 (1990); Newsom and Shaw, Weed Sci. 42:608–613 (1994); and Ahrens, Weed Technol. 4:524–528 (1990). Factors which influence the extent of herbicide injury are physiological stresses from poor seed quality, delayed emergence in cold and wet soils, seedling diseases, etc.; soil pH and climatic conditions (i.e. temperature and humidity) when applications are made; and injury from prior applications of chemicals (e.g. insecticides and other herbicides).

Glyphosate, which belongs to a different class of herbicide and is the active ingredient in both Roundup™ and Roundup Ultra™, complements activity of the other herbicides (e.g. 2,4-D and dicamba). In some cases, glyphosate interacts synergistically with these other herbicides when they are applied in combination, as shown in Moshier, Weed Sci. 28:722–724 (1980) and Flint and Barrett, Weed Sci. 37:12–18 (1989). Tank mixing Classic™ at 0.5 oz/A or Pinnacle™ at 0.125 oz/A with Roundup™ at 16 fl oz/A increases control of broadleaf weeds but, in the case of Pinnacle™, injury of Roundup Ready™ soybean is greater with the combination than with Roundup™ alone as discussed in Lich and Renner, Proc. NCWSS 50:124 (1995). Combination of Roundup Ultra™ with Synchrony™ (premix of chlorimuron plus thifensulfuron at elevated rates) effectively controls a broad spectrum of weeds.

For a number of technical and practical reasons, resistance to herbicides in agronomically important crops was among the first traits to which recombinant DNA technology and novel genetic approaches were applied. The advent of Roundup Ready™ (RR) Soybeans which have a level of resistance to glyphosate, and Liberty Link™ (LL) Soybeans which have a level of resistance to the herbicide glufosinate has provided new opportunities in agriculture. This technology has allowed developers of soybean varieties to build herbicide selectivity and true crop safety mechanisms into soybean. This approach thus has expanded the utility of proven, previously non-selective, broad spectrum herbicides. These herbicide resistant crops enable improved weed control and greater flexibility in herbicide application, resulting in better production systems. New herbicide resistance traits can be developed as components of new weed control systems featuring herbicides with the beneficial environmental characteristics needed to meet current and future rigorous demands on active ingredients.

A major obstacle to $F_1$ hybrid soybean seed production is the intensive hand-labor requirement for large numbers of pollinations. Significant heterosis was observed in Production and Performance of Hybrid Soybeans, Nelson, R., et al., Crop Science (1983) p. 549, even though relatively few hybrids were tested and the parents were unselected for combining ability. The inability to produce large quantities of hybrid seeds economically is the major barrier to the use of commercial hybrid soybean cultivars.

SUMMARY OF THE INVENTION

A process is provided for the efficient production of seeds capable of growing $F_1$ hybrid *Glycine max* comprising:

a) planting seed of a male sterile female parent line, having a male sterile gene linked to a herbicide resistance gene, adjacent to seed of a male fertile male soybean variety;

b) allowing male sterile female soybean plants to cross-pollinate with male fertile soybean plants with the aid of pollen-carrying insects;

c) spraying with said herbicide to kill non-resistant pollen and plants; and d) harvesting $F_1$ hybrid soybean seed.

It is an aspect of the present invention to develop male sterile female parent lines having a nuclear male sterile gene linked to a herbicide resistance gene.

It is another aspect of the invention to mix seed of the male sterile parent line with another male fertile soybean variety to produce a seed mixture. This seed mixture can be planted in a production field or greenhouse to produce hybrid seed.

The invention further relates to a soybean plant having a level of resistance to glyphosate or Roundup™ herbicide or sulfonylurea or STS™ herbicide, or glufosinate or Liberty™ herbicide or protoporphyrinogen oxidase inhibitors or Acuron™ herbicides.

It is an aspect of the present invention to provide a process for producing seed capable of forming $F_1$ hybrid soybean plants using a male sterile gene linked to a herbicide resistance trait.

It is another aspect of the present invention to provide a process for maintaining male sterile soybean plants useful in the production of male fertile $F_1$ hybrid soybean plants wherein pollen-carrying bees or other insects are employed to accomplish the required pollen transfer.

It is a further aspect of the present invention to provide a process for producing seeds capable of forming $F_1$ hybrid soybean plants.

These and other aspects as well as the scope, nature, and utilization of the claimed invention will be apparent to those skilled in the art from the following detailed description and appended claims.

DETAILED DESCRIPTION OF THE INVENTION

In the description and tables which follow, a number of terms are used. In order to provide a clear and consistent understanding of the specification and claims, including the scope to be given such terms, the following definitions are provided:

Male sterile gene—As used herein, "male sterile gene" refers to any nuclear or cytoplasmic gene which confers the male sterile (MS)characteristic to the plant.

Maintainer line or seed—As used herein, "maintainer line or seed" refers to a male fertile soybean line which is then crossed onto the same or similar line having the male sterile gene. This cross produces male sterile seed.

Isoline—As used herein, "isoline" refers to a line, derived from backcrossing with a recurrent parent, but still retaining a trait of interest from the "donor" parent. For example, the isoline "A+" has the characteristics of A plus the male sterile gene linked to a gene resistance to glyphosate herbicide.

Backcrossing—As used herein, "backcrossing" refers to a process in which a breeder repeatedly crosses hybrid progeny back to one of the parents (recurrent parent), for example, a first generation hybrid $F_1$ with one of the parental genotypes of the $F_1$ hybrid.

Recurrent parent—As used herein, "recurrent parent" refers to the parent genotype which is repeatedly back-crossed to during the backcross breeding procedure.

Female line—As used herein, "female line" refers to the female parent of a hybrid.

Male line—As used herein, "male line" refers to the male parent of a hybrid.

Nuclear male sterile gene—As used herein, "nuclear male sterile gene" refers to a male sterile allele or alleles which are contained within the nucleus of the cell.

Seed Set—As used herein, "seed set" means the total number of seeds on a mature plant. For example, 50% of normal seed set for a given environment means that the male sterile plants produced 50% of the number of seeds per plant compared to what is produced or expected from male fertile (selfed) soybean plants. The seed harvested from male sterile plants are $F_1$ hybrid soybean seeds, whereas the seed harvested from selfed soybean plants are not hybrid seed but selfed seed of the soybean variety.

ALS Inhibitor—As used herein, the "ALS inhibitor" means any herbicidally effective form of sulfonylureas, triazolopyrimidine sulfonamides, imidazolinones or heteroaryl ethers including any salt thereof or other related compounds or derivatives.

Atrazine—As used herein, the term "atrazine" means any herbicidally effective form of triazine, including 6-40-N-ethyl-N'-(1-methylethyl)-1,3,5-triazine-2,4-diamine, and including any salt thereof or other related compounds or derivatives.

Glufosinate—As used herein, the term "glufosinate" means any herbicidally effective form of phosphinothricin, including any salt thereof or other related compounds or derivatives.

Glyphosate—As used herein, the term "glyphosate" means any herbicidally effective form of N-phosphonomethylglycine including any salt thereof or other related compounds or derivatives or any other 5-enolpyrunyl 3-shilkimate phosphate synthase inhibitor. Roundup™ is a glyphosate herbicide.

Herbicide Resistance—The term "herbicide resistance" means the ability to survive with agronomically acceptable injury, a concentration of herbicide that is normally lethal or extremely injurious to individual plants of a given species.

Isoxaflutole—As used herein, the term "isoxaflutole" means any herbicidally effective form of 5-cyclopropyl-4 (methane sulphonyl 1-4-thifluoromethylbenzoyl), isoxazole or other related compounds or derivatives.

Paraquat—As used herein, the term "paraquat" also known as Gramoxone™, means any effective form of 1,1'-dimethyl4,4'-bipyridinium dichloride or other related compounds or derivatives.

Protoporphyrinogen oxidase inhibitors (PPO)—As used herein, the term "protophorphyrinogen oxidase inhibitors (PPO)" means any herbicidally effective form of PPO herbicides or other related compounds or derivatives. The Acuron™ gene is a herbicide tolerance gene that conveys tolerance to a broad class of PPO herbicides.

In one preferred embodiment of the present invention, a soybean line was used which contained a nuclear recessive male sterile gene such as msMOS, ATCC accession No.209344, from U.S. Pat. No. 6,046,385. Preferably, the male sterile soybean gene should result in seed set greater than 50% of the normal seed set in a field environment, when grown in the presence of effective natural soybean pollinators, or introduced pollinators, such as the alfalfa leafcutting bee (leafcutter bee), Megachile rotundata; horn-faced bees, *Osmia cornifrons;* or orchard mason bees, *Osmia lignaria*.

Observations on the genetics and developmental reproductive biology of most of the soybean mutants have been summarized by Graybosch, R. A., et al., *Male sterility in soybean—an overview,* Am J Bot 75:144–156 1988; Palmer, R. G., et al. supra, which are incorporated herein by reference. In soybean mutants ms2 and ms3, male sterility is due to abortion of microspores caused by failure of callose dissolution at the tetrad stage. In the present invention, a similar phenomenon was observed leading to microspore abortion in a potentially new male sterile line as described in Jin, W., et al., *Genetics and cytology of a new genic male-sterile soybean (Glycine max (L.) Merr.),* Sex Plant Reprod 10:13–21; 1997, which is incorporated herein by reference.

For msMOS, the genetic data indicate that the male-sterile soybean ("ms") is genic male sterile (gms) and is controlled monogenically by a single recessive allele and is described in U.S. Pat. No. 6,046,385 which is herein incorporated by reference. Based on results of glasshouse breeding experiments, this is a completely male-sterile line. The mutation causing male-sterility occurs at a locus that differs from the already characterized ms1, ms2, ms3, ms4, ms5, and ms6 soybean lines.

The most obvious abnormalities of tapetal cells in the soybean male-sterile mutant line of the present invention were cell enlargement, the accumulation of an unidentified, densely staining material, and premature degeneration. This accumulated material, based on its staining, is suspected to be sporopollenin or its precursors. The tapetum is regarded as the site for synthesis for precursors of sporopollenin (Echlin, P., *The role of the tapetum during microsporogenesis of angiosperms. In: Heslop-Harrison J (ed) Pollen: development and physiology,* Butterworths, London, pp 41–61, 1971; Horner, H. T., Jr., et al., *Pollen wall and aperture development in Helianthus annuus (Compositae:*

*Heliantheae),* Am J Bot 65:293–309, 1978; and Nakashima, H., et al., *Histological features of anthers from normal and ms3 mutant soybean (Glycine max (L.) Merr.),* Crop Sci 24:735–739, 1984).

Table 1 lists the genic male sterile mutants other than msMOS. In many of the male-sterile mutations, abnormal tapetum activity or premature degeneration is associated with the abortion of microspores (Laser, K. D., et al., *Anatomy and cytology of microsporogenesis in cytoplasmic male sterile angiosperms,* Bot Rev 38:425–454, 1972; Gottschalk, W., et al., *The genetic control of microsporogenesis in higher plants,* Nucleus (Calcutta) 17:133–166, 1974; and Koltunow, A. M., et al., *Different temporal and spatial gene expression patterns occur during anther development,* Plant Cell 2:1201–1224, 1990). Table 1 Phenotypic expression of genic male-sterile, female-fertile mutants in soybean. The msMOS gene is the preferred male sterile gene in the method of the present invention.

TABLE 1

Phenotypic expression of genic male-sterile, female-fertile mutants in soybean. The msMOS gene is the preferred male sterile gene in the method of the present invention.

| Mutant | Tetrad/Male Sterility |
| --- | --- |
| ms1 ms1 | Failure cytokinesis, tapetum degeneration |
| ms2 ms2 | Callose retention, no microspore wall formed, tapetum degeneration |
| ms3 ms3 | Callose retention, microspore wall initiated, tapetum degeneration |
| ms4 ms4 | Failure cytokinesis, tapetum degeneration |
| ms6 ms6 | Tapetum degeneration |
| msp msp | Inconsistent, abortion occurs between premeiocyte and pollen stages |
| msMOS msMOS | Callose retention, microspore wall initiated |

To date, there is no known method in soybeans which results in a high hybrid seed set on the female parents in the production of $F_1$ hybrid soybean seed. The method of the present invention allows a seed set greater than 30% of normal seed set on the female parents. This high percentage of hybrid seed set is critical for the economical production of hybrid soybean seeds.

In another preferred embodiment of the present invention, the male sterile gene is linked to a herbicide resistance gene for glyphosate (Roundup™) to allow economically segregating the male sterile plants. The male sterile gene is a nuclear gene. Using a soybean line having the linked nuclear male sterile gene and herbicide resistance, the male sterile female parents for hybrid production method of the present invention are made. In one preferred embodiment to produce male sterile elite lines, elite soybeans were crossed onto the soybean line having the male sterile msMOS gene linked with the glyphosate resistance gene. The male sterile msMOS gene is linked to the glyphosate resistance gene with a recombination ratio of approximately 11%. These crosses were made using hand pollination procedures commonly used and known by those skilled in soybean plant breeding. In the next generation, pollen from the $F_1$ hybrid plants was crossed back to the elite female (recurrent parent). These hybrid plants are preferably sprayed with the glyphosate herbicide every ten days starting with the presence of flower buds until after pollinations are completed. The application rate should be at or just below standard recommended rates. For glyphosate herbicide, this rate is preferably 24 to 30 ounces per acre. This spray application kills the male gametes that are not carrying the herbicide resistant male sterile gene and assists in the backcrossing from the $F_1$ and continued subsequent backcrossing to the original elite female. This procedure and backcrossing preferably continues for a number of backcross generations, preferably 4–9 backcrosses (BC) until the original line has been converted to the state of a stable near isoline. After the elite female is converted to the male sterile, one then makes larger quantities of maintainer seed and the male sterile parent seed.

In the present invention, maintainer seed consists of a male fertile line which, when crossed onto the male sterile (ms) plants, produces male sterile seed. Maintainer seed is heterozygous for the ms gene (i.e., MSms) and is developed by crossing the original soybean line (recurrent parent) onto the male sterile plants of the isoline (developed from this same soybean line via the backcrossing procedure). Initially, in order to develop a male sterile isoline, this is accomplished by planting alternate rows of the original line and the segregating progeny of $F_2$ BC seed of the line for each backcross generation. This can be accomplished by hand pollination or preferably by insect pollinators of soybean with the fertile segregants of the $F_2$ BC rows being removed by hand as they begin to flower. The initial flowers on each plant are checked and tagged as male sterile or removed if fertile. This method of developing the pure male sterile isoline is a one-time procedure for a given genotype as subsequent maintainer seed is provided by crossing the original soybean line onto rows of plants of the pure male sterile isoline.

Isoline male sterile seed is produced by crossing pollen from maintainer seed onto male sterile plants from segregating $F_2$ backcrossed seed. When the selectable marker is for an herbicide, the maintainer seed plants must be sprayed with herbicide (e.g., glyphosate) as described for the $F_1$ and $F_1$ backcrosses in the line conversion process and for the same reason. As in the initial production of maintainer seed, the initial male sterile can be made by hand pollination or by insect pollinators of soybean. The fertile plants in the $F_2$ BC rows must be removed by hand as in the process of producing maintainer seed.

Subsequent pure isoline male sterile seed is produced by crossing rows of maintainer plants sprayed with herbicide as outlined previously onto rows of pure isoline male sterile plants by the presence of natural or introduced pollinators.

Several factors require the producer to adjust the rates and/or timing of the herbicide application. Depending on what herbicide is used, the environmental conditions and the genetics of the parent lines, several adjustments are required. With glyphosate, for example, the application rate generally varies from 16 to 32 ounces per acre or more. Timing between applications are adjusted from five or six days to as much as 20 days between sprayings. In addition, the first spraying is typically timed with the presence of the first flower buds on the plants, but earlier spraying applications may be used to increase the effectiveness of spraying techniques.

With quantities of male sterile seed capable of setting economically adequate rates of production one can proceed to produce hybrid soybean seed. If the male soybean line used to produce the hybrid does not carry the same herbicide resistance as the male sterile female (glyphosate resistant female) the seed can be preferably blended approximately 30% male and 70% female (30/70) before planting in the production field. Depending on growing conditions and pollinator activity, it may be necessary to vary the ratio of male to female seed parents in a production field from 30/70 to 40/60 or 50/50 and even higher amounts of male seed. Natural or introduced pollinators (in the case of alfalfa leafcutting bees use approximately 10,000 to 20,000 per acre with a shelter placed in each 4 to 10 acres) are needed to move pollen from the male plants to the male sterile female plants.

In one embodiment, the production field is sprayed with the herbicide to which the female is resistant (glyphosate) at approximately the maximum recommended rate immediately at the end of the flowering period. This eliminates having any male seed in the conditioned hybrid seed production. If the female is not herbicide resistant or does not have resistance different than the male, the production field is planted in alternate rows or male female patterns, such as one to two or one to three, and the male rows are removed or kept separate from the female hybrid seed parent.

Sterile off-type plants in hybrid soybeans may set little or no seed and may be considered more detrimental in soybeans than in a crop such as corn where male sterile plants set normally when mixed with fertile plants. When there is concern about off-types or non-hybrid plants coming from either the male or female parents, they can be reduced by various means. When the male is carrying herbicide resistance different than the female then methods are available to reduce off-type plants. For example, if the male has resistance to STS and the female is susceptible, then the seed can be treated with the herbicide to which the female is susceptible, Chlorsulfuron, when processed in the seed conditioning facilities. This renders any female selfs or off-types as non-competitive (few or no seed produced on these plants) in the growers production field. Another method to have pure production for the grower when the male and female parents of the hybrid have different herbicide resistance; is to spray the fields shortly after emergence with one or the other, or both herbicides to remove at the seedling stage off type plants originating from the male, female or both as the situation allows.

These processes and procedures when integrated as described allow for the development and production of hybrid soybean seed on an economically viable basis.

The present invention is a method for forming seeds capable of yielding $F_1$ hybrid soybean plants (i.e., hybrid soybean plants of the first filial generation) or maintaining male sterile soybean plants useful in the production of male fertile $F_1$ hybrid soybean plants. Male sterile (i.e., seed parents) and the male fertile soybean plants (i.e., pollen parents) are caused to undergo cross-pollination with the aid of pollen-carrying bees. In accordance with one embodiment of the present invention the pollen-carrying bees (e.g., leafcutter bees) facilitates a high level of cross-pollination and seeds are formed on the male sterile soybean plants which ultimately are harvested.

In one aspect of the invention, the female seed parents often retain green leaves after the hybrid seed on the plants is physiologically mature. Physiological maturity generally occurs when the soybean seeds have turned from a green to yellow color. By spraying a defoliant such as paraquat on the female seed plants the green leaves die and are removed approximately 2 or 3 weeks sooner than would naturally occur. This allowed for an earlier harvest (14–20 days), aided the ease of combine harvesting because of better dry down of the plants, and created better seed quality because of the lessened exposure to the elements that the mature seed experienced.

In another aspect of the invention, the female seed parents and male pollinator are harvested together in order to create a hybrid blend. Under normal pollinating conditions this results in a blend that is approximately 70% inbred seed and 30% hybrid seed. The hybrid seed found on the female seed parents is often 20–30% larger than the inbred seed. By screening out up to 35% of the smaller inbred seed, the percentage of hybrid in the blend is shifted towards 40% rather than 30%. For example, a hybrid production field is harvested without removing the male seed parent and results in a hybrid blend containing 70% inbred (male seed parent) and 30% hybrid seed. The seed conditioner may remove a majority of the smaller seeds from the blend. These smaller seeds are nearly all from the male seed parent (inbred line). If the smallest 25% of the total blend is removed through screening, then the resulting blend is, for example, approximately 60% inbred and 40% hybrid seed. This screening method can shift the ratio of inbred to hybrid towards the hybrid component in any blend regardless of the percentages present in the initial harvesting.

Using similar techniques and other techniques well known in the art, other male sterile genes and herbicide resistance genes can also be used in the present invention. The instant invention relates to herbicide resistance genes, constructs, promoters and male sterility genes and to methods of incorporating the resistance and male sterile genes into commercial soybean varieties. Suitable genes, promoters and methods may be found in *Herbicide-Resistant Crops,* Editor Stephen O. Duke, CRC Lewis Publishers, 1996; *Herbicide Resistance in Plants,* Editors Stephen B. Powles and Joseph A. M. Holtum, CRC Press Inc., 1994; and in U.S. Pat. Nos. 5,084,082; 5,359,142; 5,322,938; 5,424,200; 5,164,316; 5,352,605; 5,094,945; 4,535,600 and 4,940,835, all of which are incorporated herein by reference.

As used herein, the term "plant" includes plant cells, plant protoplasts, plant cells of tissue culture from which soybean plants can be regenerated, plant calli, plant clumps, and plant cells that are intact plants or parts of plants such as pollen, flowers, seeds, leaves, stems and the like.

EXAMPLES

The following examples are provided to further illustrate the present invention and are not intended to limit the invention beyond the limitations set forth in the appended claims.

EXAMPLE 1

Development of msMOS Gene Linked with Glyphosate Gene

In the Summer of 1997 Midwest Oilseeds line 607245, a conventional line containing the male sterile gene, was crossed with 61615-CC-234, a Roundup-Ready™ soybean line. The $F_1$ population was grown in Homestead, Fla. in the Winter of 1997–1998, where it was sprayed with Roundup™ every two weeks throughout the flowering period. The $F_2$ population was replanted at Homestead in February, 1998 and was also sprayed with Roundup™ throughout flowering. If the male sterility was independent from the Roundup™ gene, it was expected the $F_2$ populations would contain approximately 25% sterile plants. The $F_2$ populations were approximately 5.5% male sterile which indicated the two genes (ms and Roundup™ resistance) were linked with a recombination ratio of approximately 11%, since half of the recombinants are as sterile plants. Two hundred of the fertile plants were harvested individually and were planted at Adel, Iowa in the Summer of 1998.

Different Roundup Ready™ gene events can be developed which are more closely linked to the male sterile gene than 11%. A very tight linkage would result in a recombination ratio of 0%. Following the same technique as discussed in the previous paragraph, an $F_2$ population containing less than 5% sterile plants would indicate a closer linkage between the male sterile gene and the same or a different Roundup Ready™ gene or event. In addition, this method is not specific to Roundup™ herbicide resistance. This same technique can be used with other herbicide resistant genes (such as genes for resistance to glufosinate, STS, isoxaflutole or PPO) to determine if they are linked to a male sterile gene. This same method is used for other male sterile genes, for example msMOS, ms1, ms2, ms3, ms4, ms6 and msp.

EXAMPLE 2

Herbicide resistance genes are introduced individually or in combination into plant genomes by a variety of methods. One preferred means of gene introduction is the use of microprojectile bombardment. For example, a gene for herbicide tolerance, such as the CP4 EPSPS conferring tolerance to glyphosate is placed under the control of a promoter such as the Cauliflower Mosaic Virus (CaMV) 35S promoter. The promoter and a nontranslated leader sequence such as the alfalfa mosaic virus, tobacco mosaic virus, or cucumber mosaic virus leader, is fused to the 5' end of the gene. A promoter such as the CaMV 35S promoter has its activity enhanced by duplication of a portion of the promoter sequence. A transcription termination sequence such as the CaMV 35S terminator or the nopaline synthase (nos) terminator is fused to the gene at the 3' end. Methods for accomplishing these constructions are well known in the art. This construction is introduced into an *E. coli* plasmid for propagation and for transformation. This plasmid also contains a marker gene such as the gus marker—a gene well known in the art, encoding the enzyme β-glucuronidase, whose expression in plant tissues allows the in situ visual identification of cells which have received the transforming DNA.

DNA of the construct described above is introduced into plant genomes by precipitation onto microscopic gold or tungsten particles and acceleration of these particles into plant tissue by means of a device such as the DuPont PDS 1000, a commercially available device for conducting plant transformations by means of microprojectile bombardment. Methods for accomplishing this are well known in the art. Plant tissue such as embryogenic callus or shoot meristems are chosen as the target for bombardment. These tissues are arranged in a petri dish in such a way as to offer the best possibility of successful transformation. Parameters are well-known in the art, but modifications and adjustments must be made in these parameters to optimize the transformation of each species. The particles coated with DNA are spread on a disc of mylar, which is loaded into the microprojectile apparatus. The mylar disc is accelerated until its flight is impeded by a stopping screen. The disc is stopped, but the particles continue their progress through the apparatus until they become embedded in the target plant tissue.

Selection of transformed tissue and then regeneration of these tissues into whole plants are accomplished by various methods. Some use the gene conferring herbicide tolerance to select plant cells which have incorporated the DNA, others make use of the accompanying gus gene as an indicator of transformation events, and then physically selecting or isolating transformed tissue. Such methods are well described in the literature. Methods for regenerating transformed tissue into whole plants are well-known in the art; especially known are the parameters which must be adjusted for each species or genotype in order to achieve efficient rates of regeneration.

Genes conferring a level of resistance to herbicides, such as glyphosate and glufosinate, are introduced in combination by constructing them separately, mixing the constructs, and then precipitating them together onto the same gold or tungsten particles. This method depends upon the ability to select for cells which have received all of the genes of interest. Double selection is applied, exposing the cells to both herbicides simultaneously or in sequence, thus allowing the survival only of those cells which have incorporated both herbicide tolerance genes. Assaying for gus gene activity is also used in combination, if only one of the constructs is made in tandem with the gus gene. In situ assays are made of tissues which are expressing gus, and those tissues are then physically isolated. Selection is then imposed on those tissues by application of the herbicide for which resistance is encoded by the gene which was not constructed in tandem with gus. The order is also reversed, i.e. selection may be imposed first, followed by gus assays.

Alternatively, the genes are introduced together by introducing them into the same $E.$ $coli$ plasmid, with or without a gus marker gene. Each gene is under the control of its own promoter, untranslated leader (if appropriate), and 3' terminator region as described above, and inserted into appropriate cloning sites in the transformation vector. After microprojectile bombardment, selection of transformed tissue and subsequent regeneration into plants is then accomplished by physical selection of transformed tissue identified in situ via gus assays. In addition, selection is imposed by exposure of the cells to one or both herbicides, either simultaneously or sequentially.

The above illustration of the means by which genes can be combined in transformations describe methods well known in the art. They are provided as examples only, and are not meant to be an exhaustive description of the various means by which genes can be introduced into plant genomes. Other methods, such as electroporation, aerosol-beam, Agrobacterium-mediated transformation, or other methods may be used to obtain the desired results.

EXAMPLE 3

Selection of Herbicide Genes Linked with Male Sterile Genes

Additional herbicide resistance traits and/or male sterile genes are incorporated into the hybrid soybean production method of the present invention by using several methods. For example, a male sterile soybean line is crossed with a fertile but herbicide resistant soybean line (e.g., resistant to Liberty™). The $F_1$ population is grown and sprayed with the Liberty™ herbicide at regular intervals throughout the flowering period. The $F_2$ population may be replanted and also sprayed with Liberty™ herbicide throughout flowering. If male sterility is independent of the Liberty™ gene, the $F_2$ population contains approximately 25% sterile plants. If sterility and herbicide resistance are closely linked, the $F_2$ population contains nearly 0% sterile plants, and with only one-half of the recombinants in the populations showing the male sterile phenotype.

In another example, a new male sterile soybean line is crossed with a fertile but herbicide resistant soybean line (resistant to Roundup™, for example). The $F_1$ population is grown in a nursery and sprayed with Roundup™ herbicide at regular intervals throughout flowering. The $F_2$ population is replanted and also sprayed with Roundup™ herbicide throughout flowering. If male sterility is independent of the Roundup™ gene, the $F_2$ population contains approximately 25% sterile plants. If sterility and herbicide resistance are closely linked, the $F_2$ population contains nearly 0% sterile plants, with only one-half of the recombinants in the populations showing the male sterile phenotype.

EXAMPLE 4

Development of Male Sterile 501577-37 Line

In one preferred embodiment, commercial hybrid production utilizes Roundup-Ready™ male sterile lines that have been backcrossed 6 or 7 generations to conventional elite lines as the female seed parent. Fewer generations of backcrossing are necessary to proceed with production for testing purposes. Up to four backcross generations per year can be obtained through the use of greenhouse and winter nursery facilities.

In July 1998, elite line 501577-37 was crossed with Roundup™ (i.e., glyphosate) resistant male sterile plant 02-02-1 having the msMOS gene linked to the Roundup™ resistance gene. 501577-37 has a relative maturity of 0.9. The $F_1$ progeny (BCO) from these crosses were grown in Puerto Rico in the Winter of 1998–99 and sprayed with Roundup at a rate of one quart per acre every 10 days throughout flowering. Pollen taken from the $F_1$ plants was backcrossed to elite line 501577-37. The $F_1$ progeny ($BC_1$) from the winter crosses were grown in Iowa in the Summer of 1999. The $F_1$ plants were sprayed with one quart per acre of Roundup™ every 10 days. Pollen from the $BC_1$ $F_1$'s was backcrossed to elite line 501577-37 creating a $BC_2$. The cycle of backcrossing and spraying is repeated 1–4 or more times to produce a male sterile 501577-37 line.

EXAMPLE 5

Development of Male Sterile 506521-73 Line

In July 1998, elite line 506521-73 was crossed with Roundup™ (i.e., glyphosate) resistant male sterile plant 15-05-2 having the msMOS gene linked to the Roundup™ resistance gene. 506521-73 has a relative maturity of 3.0. The $F_1$ progeny (BCO) from these crosses were grown in Puerto Rico in the Winter of 1998–1999 and sprayed with Roundup™ at a rate of one quart per acre every 10 days throughout flowering. Pollen taken from the $F_1$ plants was used to backcross to elite line 506521-73. The $F_1$ progeny ($BC_1$) from the winter crosses were grown in Iowa in the Summer of 1999. The $F_1$ plants were sprayed with one quart per acre of Roundup™ every 10 days. Pollen from the $BC_1$ $F_1$'s was backcrossed to elite line 506521-73 creating an additional backcross or $BC_2$. The cycle of backcrossing and spraying is repeated 1–4 or more times to produce a male sterile 506521-73 line.

EXAMPLE 6

Development of Male Sterile 512630-64-51 Line

In July 1998, elite line 512630-64-51 was crossed with Roundup™ (i.e., glyphosate) resistant male sterile plant 05-01-1 having the msMOS gene linked to the Roundup™ resistance gene. 512630-64-51 has a relative maturity of 3.8. The $F_1$ progeny (BCO) from these crosses were grown in Puerto Rico in the Winter of 1998–99 and sprayed with Roundup™ at a rate of one quart per acre every 10 days throughout flowering. Pollen taken from the $F_1$ plants was backcrossed to elite line 512630-64-51. This progeny ($BC_1$)

from the winter crosses were grown in Iowa in the Summer of 1999. The $F_1$ plants were sprayed with one quart per acre of Roundup every 10 days. Pollen from the $BC_1$ $F_1$'s was backcrossed to elite line 512630-64-51 creating an additional backcross, or $BC_2$. The cycle of backcrossing and spraying is repeated 1–4 or more times to produce a male sterile 512630-64-51 line.

EXAMPLE 7

Development of Male Sterile 30148-49 Line

In July 1998, elite line 30148-49 was crossed with Roundup™ (i.e., glyphosate) resistant male sterile plants 05-06-1 having the msMOS gene linked to the Roundup™ resistance gene. 30148-49 has a relative maturity of 1.9. The $F_1$ progeny (BCO) from these crosses were grown in Puerto Rico in the early Winter, 1998–99 and sprayed with Roundup™ at a rate of one quart per acre every 10 days throughout flowering. Pollen taken from the $F_1$ plants was backcrossed to elite line 30148-49. The $F_1$ progeny ($BC_1$) from the early winter crosses were replanted in Puerto Rico in February of 1999. The $F_1$ plants were sprayed with one quart per acre of Roundup™ every 10 days. Pollen from the $BC_1$ $F_1$'s was backcrossed to elite line 30148-49 creating an additional backcross or $BC_2$. The same techniques were repeated in Iowa over the Summer of 1999 to create $BC_3$ $F_1$'s. The cycle of backcrossing and spraying is repeated 1–4 or more times to produce a male sterile 30148-49 line.

EXAMPLE 8

Development of Male Sterile 505478-32 Line

In July 1998, elite line 505478-32 was crossed with Roundup™ (i.e., glyphosate) resistant male sterile plant 19-07-1 having the msMOS gene linked to the Roundup™ resistance gene. 505478-32 has a relative maturity of 2.4. The $F_1$ progeny (BCO).from these crosses were grown in Puerto Rico in the early Winter, 1998–99 and sprayed with Roundup™ at a rate of one quart per acre every 10 days throughout flowering. Pollen taken from the $F_1$ plants was backcrossed to elite line 505478-32. The $F_1$ progeny ($BC_1$) from the early winter crosses were replanted in Puerto Rico in February of 1999. We again sprayed the $F_1$ plants with one quart per acre of Roundup™ every 10 days. Pollen from the $BC_1$ $F_1$'s was backcrossed to elite line 505478-32 creating an additional cross, or $BC_2$. The same techniques were repeated in Iowa over the Summer of 1999 to create $BC_3$ $F_1$'s. The cycle of backcrossing and spraying is repeated 1–4 or more times to produce a male sterile 505478-32 line.

EXAMPLE 9

Development of Male sterile 22581-64 Line

In July 1998, elite line 22581-64 was crossed with Roundup™ (i.e., glyphosate) resistant male sterile plant 06-06-1 having the msMOS gene linked to the Roundup™ resistance gene. 22581-64 has a relative maturity of 2.4 and is resistant to STS herbicide. The $F_1$ progeny (BCO) from these crosses were grown in Puerto Rico in the early Winter, 1998–99 and sprayed with Roundup™ at a rate of one quart per acre every 10 days throughout flowering. Pollen taken from the $F_1$ plants was backcrossed to elite line 22581-64. The $F_1$ progeny ($BC_1$) from the early winter crosses were replanted in Puerto Rico in February of 1999. We again sprayed the $F_1$ plants with one quart per acre of Roundup™ every 10 days. Pollen from the $BC_1$ $F_1$'s was backcrossed to elite line 22581-64 creating a $BC_2$. The same techniques were repeated in Iowa over the Summer of 1999 to create $BC_3$ $F_1$'s. The cycle of backcrossing and spraying is repeated 1–4 or more times to produce a male sterile 22581-64 line.

EXAMPLE 10

Development of Male Sterile 413735-11-42 Line

In July 1998, elite line 413735-11-42 was crossed with RoundUp™ (i.e., glyphosate) resistant male sterile plant 03-06-1 having the msMOS gene linked to the RoundUp™ resistance gene. 413735-11-42 has a relative maturity of 2.4. The $F_1$ progeny (BCO) from these crosses were grown in Puerto Rico in the early Winter, 1998–99 and sprayed with Roundup™ at a rate of one quart per acre every 10 days throughout flowering. Pollen taken from the $F_1$ plants was backcrossed to elite line 413735-11-42. The $F_1$ progeny ($BC_1$) from the early winter crosses were replanted in Puerto Rico in February of 1999. The $F_1$ plants were sprayed with one quart per acre of Roundup™ every 10 days. Pollen from the $BC_1$ $F_1$'s was backcrossed to elite line 413735-11-42 creating a $BC_2$. The same techniques were repeated in Iowa over the Summer of 1999 to create $BC_3$ $F_1$'s. The cycle of backcrossing and spraying is repeated 1–4 or more times to produce a male sterile 413735-11-42 line.

EXAMPLE 11

Production of Maintainer 501577-37

In February 2000 $F_2$ seed was harvested from $BC_1$ $F_1$ plants growing in the greenhouse at Adel, Iowa. These plants were a $BC_2$ of elite line 501577-37 with maturity of 0.9. In Homestead, Fla. we planted line 501577-37 with 72 inches of space between the rows. These rows serve as borders of male pollinator. In between the male borders (36 inches from each row) two seeds of 501577-37 (male) were planted in a hill followed by one $F_2$ seed from a single $BC_2$ $F_1$ plant (female) in another hill. The spacing between hills is approximately one foot. The male and female hills were alternated across the entire plot. The first 50 female hills used $F_2$ seed from a single $BC_2$ $F_1$ plant. The next 50 females came from a different $BC_2$ $F_1$ single plant . . . and so on up the field. Alfalfa leafcutter bees were used at a rate of 10,000 bees per acre to pollinate the plot. Seed harvested from the male sterile female plants is a $BC_3$ maintainer of line 501577-37.

EXAMPLE 12

Maintainer for 506521-73

In February, 2000 $F_2$ seed was harvested from $BC_2$ $F_1$ plants growing in the greenhouse at Adel, Iowa. These plants were a $BC_2$ of elite line 506521-73 with maturity of 3.0. In Homestead, Fla. we planted line 506521-73 with 72 inches of space between the rows. These rows serve as borders of male pollinator. In between the male borders (36 inches from each row) two seeds of 506521-73 (male) were planted in a hill followed by one $F_2$ seed from a single $BC_2$ $F_1$ plant (female) in another hill. The spacing between hills is approximately 1 foot. The male and female hills were alternated across the entire plot. The first 50 female hills used $F_2$ seed from a single $BC_2$ $F_1$ plant. The next 50 females came from a different $BC_2$ $F_1$ single plant . . . and so on up the field. Alfalfa leafcutter bees were used at a rate of 10,000 bees per acre to pollinate the plot. Seed harvested from the male sterile female plants is a BC3 maintainer of line 506521-73.

EXAMPLE 13

Maintainer for 512630-64-51

In February, 2000 $F_2$ seed was harvested from $BC_2$ $F_1$ plants growing in the greenhouse at Adel, Iowa. These plants were a $BC_2$ of elite line 512630-64-51 with maturity of 3.8. In Homestead, Fla. we planted line 512630-64-51 with 72 inches of space between the rows. These rows serve as borders of male pollinator. In between the male borders (36 inches from each row) two seeds of 512630-64-51 (male) were planted in a hill followed by one $F_2$ seed from a single $BC_2$ $F_1$ plant (female) in another hill. The spacing between hills is approximately one foot. The male and female hills were alternated across the entire plot. The first 50 female hills used $F_2$ seed from a single $BC_2$ $F_1$ plant. The next 50 females came from a different $BC_2$ $F_1$ single plant . . . and so on up the field. Alfalfa leafcutter bees were used at a rate of 10,000 bees per acre to pollinate the plot. Seed harvested from the male sterile female plants is a $BC_3$ maintainer of line 512630-64-51.

EXAMPLE 14

Maintainer for 30148-49

In February 2000 $F_2$ seed was harvested from $BC_3$ $F_1$ plants growing in the greenhouse at Adel, Iowa. These plants were a $BC_3$ of elite line 30148-49 with maturity of 1.9. In Homestead, Fla. we planted line 30148-49 with 72 inches of space between the rows. These rows serve as borders of male pollinator. In between the male borders (36 inches from each row) two seeds of 30148-49 (male) were planted in a hill followed by one $F_2$ seed from a single $BC_3$ $F_1$ plant (female) in another hill. The spacing between hills is approximately one foot. The male and female hills were alternated across the entire plot. The first 50 female hills used $F_2$ seed from a single $BC_3$ $F_1$ plant. The next 50 females came from a different $BC_3$ $F_1$ single plant . . . and so on up the field. Alfalfa leafcutter bees were used at a rate of 10,000 bees per acre to pollinate the plot. Seed harvested from the male sterile female plants is a $BC_4$ maintainer of line 30148-49.

EXAMPLE 15

Maintainer for 505478-32

In February, 2000 $F_2$ seed was harvested from $BC_1$ $F_1$ plants growing in the greenhouse at Adel, Iowa. These plants were a $BC_3$ of elite line 505478-32 with maturity of 2.4. In Homestead, Fla. we planted line 505478-32 with 72 inches of space between the rows. These rows serve as borders of male pollinator. In between the male borders (36 inches from each row) two seeds of 505478-32 (male)were planted in a hill followed by one $F_2$ seed from a single $BC_3$ $F_1$ plant (female) in another hill. The spacing between hills is approximately one foot. The male and female hills were alternated across the entire plot. The first 50 female hills used $F_2$ seed from a single $BC_3$ $F_1$ plant. The next 50 females came from a different $BC_3$ $F_1$ single plant . . . and so on up the field. Alfalfa leafcutter bees were used at a rate of 10,000 bees per acre to pollinate the plot. Seed harvested from the male sterile female plants is a $BC_4$ maintainer of line 505478-32.

EXAMPLE 16

Maintainer for 22581-64

In February, 2000 $F_2$ seed was harvested from BC3 $F_1$ plants growing in the greenhouse at Adel, Iowa. These plants were a $BC_3$ of elite line 22581-64 which has a maturity of 2.4 and is resistant to STS herbicide. In Homestead, Fla. we planted line 22581-64 with 72 inches of space between the rows. These rows serve as borders of male pollinator. In between the male borders (36 inches from each row) two seeds of 22581-64 (male) were planted in a hill followed by one $F_2$ seed from a single $BC_3$ $F_1$ plant (female) in another hill. The spacing between hills is approximately one foot. The male and female hills were alternated across the entire plot. The first 50 female hills used $F_2$ seed from a single $BC_3$ $F_1$ plant. The next 50 females came from a different $BC_3$ $F_1$ single plant . . . and so on up the field. Alfalfa leafcutter bees were used at a rate of 10,000 bees per acre to pollinate the plot. Seed harvested from the male sterile female plants is a $BC_4$ maintainer of line 22581-64.

EXAMPLE 17

Maintainer for 413735-19-79

In February 2000 $F_2$ seed was harvested from $BC_3$ $F_1$ plants growing in the greenhouse at Adel, Iowa. These plants were a $BC_3$ of elite line 413735-19-79 with maturity of 2.4. In Homestead, Fla. we planted line 413735-19-79 with 72 inches of space between the rows. These rows serve as borders of male pollinator. In between the male borders (36 inches from each row) two seeds of 413735-19-79 (male) were planted in a hill followed by one $F_2$ seed from a single $BC_3$ $F_1$ plant (female) in another hill. The spacing between hills is approximately one foot. The male and female hills were alternated across the entire plot. The first 50 female hills used $F_2$ seed from a single $BC_3F_1$ plant. The next 50 females came from a different $BC_3$ $F_1$ single plant . . . and so on up the field. Alfalfa leafcutter bees were used at a rate of 10,000 bees per acre to pollinate the plot. Seed harvested from the male sterile female plants is a $BC_4$ maintainer of line 413735-19-79.

EXAMPLE 18

In the Winter of 1998–1999 male border rows of elite line 34606-S5 were planted in Chacabuco, Argentina. In between the male border rows one row was planted in which line 34606-S5 (male) was alternated with line RS9805-2, which was segregating 25% sterile (female). The alternating row was planted male, female, male, female and so on. At maturity, the male sterile plants were harvested from the alternating rows. The seed from these sterile plants was a hybrid of lines 34606-S5 and RS9805-2. Three replications of this hybrid were planted in a yield trial at Adel, Iowa in the Summer of 1999. The yield trial data is shown in Table 2.

EXAMPLE 19

In the Winter of 1998–1999 male border rows of elite line 18270-95 were planted in Chacabuco, Argentina. In between the male border rows one row was planted in which line 18270-95 (male) was alternated with line RS9811-2, which was segregating 25% sterile (female). The alternating row was planted male, female, male, female and so on. At maturity, the male sterile plants were harvested from the alternating rows. The seed from these sterile plants was a hybrid of lines 18270-95 and RS9811-2.

EXAMPLE 20

In the Winter of 1998–1999 male border rows of elite line 615741 were planted in Chacabuco, Argentina. In between the male border rows one row was planted in which lines 615741 (male) was alternated with line RS9811-2, which was segregating 25% sterile (female). The alternating row was planted male, female, male, female and so on. At maturity, the male sterile plants were harvested from the alternating rows. The seed from these sterile plants was a hybrid of lines 615741 and RS9811-2.

EXAMPLE 21

1999 Hybrid Yield Data

As shown in Table 2, the hybrids used in this trial were made in Argentina in the winter of 1998–1999 using the methods of the present invention. Each plot consisted of two ten-foot rows which were planted 6 seeds per foot. As shown in Table 2, the average weight for the hybrid soybean lines was higher than the parental lines (i.e., the elite soybean lines or the fertile sister lines).

The yield trial results shown in Table 2 contain two replications of elite line 34606-S5 which had a harvested seed weight of 3.17 and 3.88 pounds respectively. The trial also contained three replications of a hybrid of 34606-S5 and various male sterile sister lines (RS9805-2, 5-6; RS9808-1; and RS9809-9, 10–4). The hybrid plots had an average harvested weight of 4.10 pounds. The three 100% fertile sister lines included in the trial possessed the same pedigree as the male sterile lines used to make the hybrids in Argentina. These 100% fertile sister lines, however did not receive a copy of the male sterile gene when the $F_1$ population was segregating. They were included in the trial as a yield check and had an average harvested weight of 2.89 pounds.

TABLE 2

| Entry | Relative Maturity | Harvested Seed Weight/Plot | Average Weight |
|---|---|---|---|
| Elite Line | | | |
| 34606-S5 | 3.3 | 3.17 | |
| 34606-S5 | 3.3 | 3.88 | 3.53 |
| Hybrid Line | | | |
| F1 34606-S5 * RS9805-2, 5-6 | 3.5 | 3.86 | |
| F1 34606-SS * RS9808-1 | 3.5 | 4.28 | |
| F1 34606-S5 * RS9809-9, 10-4 | 3.5 | 4.17 | 4.10 |
| 100% Fertile Sister Lines | | | |
| RS9805-5 | 3.5 | 2.90 | |
| RS9809-10 | 4.0 | 2.50 | |
| RS9809-2 | 3.0 | 3.27 | 2.89 |

EXAMPLE 22

Seed Set on Sterile and Fertile Plants

The data in Table 3 was collected in the Summer of 1999 from sterile and fertile plants of RS9809-3 harvested in Osceola, Ark. The sterile plants have the msMOS gene linked with the RoundUp™ resistance gene. Native leafcutter bees were the only known pollinator present. The average seed set on the sterile plants was 61.8% of the average set from the fertile plants.

TABLE 3

| Plant # | # Seeds on Sterile Plants | # Seeds on Fertile Plants |
|---|---|---|
| 1 | 57 | 153 |
| 2 | 116 | 282 |

TABLE 3-continued

| Plant # | # Seeds on Sterile Plants | # Seeds on Fertile Plants |
|---|---|---|
| 3 | 98 | 216 |
| 4 | 152 | 75 |
| 5 | 127 | 322 |
| 6 | 95 | 256 |
| 7 | 143 | 175 |
| 8 | 186 | 232 |
| 9 | 172 | 122 |
| 10 | 168 | 293 |
| TOTAL | 1314 | 2126 |

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A method of producing hybrid soybean seed comprising:
   a) planting seed of a male sterile female parent line, having a male sterile gene linked to a herbicide resistance gene, adjacent to seed of a male fertile male soybean variety;
   b) allowing male sterile female soybean plants to cross-pollinate with male fertile soybean plants with the aid of pollen-carrying insects;
   c) spraying said plants with said herbicide to kill non-resistant pollen and plants; and
   d) harvesting $F_1$ hybrid soybean seed.

2. A method for the efficient production of seeds capable of growing male fertile $F_1$ hybrid *Glycine max* plants according to claim 1, wherein said male sterile soybean plants of step a) contain a nuclear male sterile gene.

3. The male sterile gene of claim 2, wherein said gene is selected from the group consisting of: msMOS, ms1, ms2, ms3, ms4, ms6 and msp.

4. The method of claim 1, wherein said herbicide is selected from the group consisting of: glyphosate, glufosinate, isoxaflutole, ALS inhibitors, and protoporphyrinogen oxidase inhibitors.

5. A method for the efficient production of seeds capable of growing male fertile $F_1$ hybrid *Glycine max* plants according to claim 1, wherein said male fertile soybean plants grown in step a) are a pure line variety.

6. A method for the efficient production of seeds capable of growing male fertile $F_1$ hybrid *Glycine max* plants according to claim 1, wherein said seed is planted as a mixture of male sterile parent line and a male fertile soybean variety.

7. The method of claim 1, wherein seed of said male sterile female parent line is planted in separate rows in the field from said male fertile soybean variety.

8. A method for the efficient production of seeds capable of growing male fertile $F_1$ hybrid *Glycine max* plants according to claim 1, wherein said pollen-carrying insects of step b) are primarily leafcutter bees.

9. A method for the efficient production of seeds capable of growing male fertile $F_1$ hybrid *Glycine max* plants according to claimy 1, wherein a supplemental pollen source for said pollen-carrying insects is provided in addition to the pollen formed on said male fertile soybean plants of step a) in order to provide ample pollen to support said pollen-carrying insects.

10. A method for the efficient production of seeds capable of growing male fertile $F_1$ hybrid *Glycine max* plants according to claim 1, wherein said herbicide resistance gene is resistant to a herbicide selected from the group consisting of: glyphosate, sulfonylurea, glufosinate or protoporphyrinogen oxidase inhibitors.

11. The method of claim 1, wherein said herbicide resistance is glyphosate and said male sterile gene is msMOS.

12. The method of claim 1, wherein seed set on said male sterile plants is greater than 30%.

13. The method of claim 12, wherein said seed set is between about 30% and about 40%.

14. The method of claim 12, wherein said seed set is between about 41% and about 50%.

15. The method of claim 12, wherein said seed set is between about 51% and about 60%.

16. The method of claim 12, wherein said seed set is between about 61% and about 70%.

17. The method of claim 12, wherein said seed set is between about 71% and about 80%.

18. The method of claim 12, wherein said seed set is between about 81% and about 90%.

19. A method of producing soybean F1 hybrid seed comprising:
   a) planting seed of a male sterile female parent, having a male sterile gene linked to a herbicide resistance gene, adjacent to seed of a male-fertile male soybean variety having resistance to a different herbicide;
   b) allowing male sterile female soybean plants to cross with male fertile male plants with the aid of pollen-carrying insects;
   c) spraying said plants after the end of the flowering period with said herbicide to which said female is resistant;
   d) harvesting $F_1$ hybrid soybean seed.

20. A method for the efficient production of seeds capable of growing male fertile $F_1$ hybrid *Glycine max* plants according to claim 19, wherein said male sterile soybean plants of step a) contain a nuclear male sterile gene.

21. The male sterile gene of claim 20, wherein said gene is selected from the group consisting of: msMOS, ms1, ms2, ms3, ms4, ms6 and msp.

22. The method of claim 19, wherein said herbicide is selected from the group consisting of: glyphosate, glufosinate, isoxaflutole, ALS inhibitors, and protoporphyrinogen oxidase inhibitors.

23. A method for the efficient production of seeds capable of growing male fertile $F_1$ hybrid *Glycine max* plants according to claim 19, wherein said pollen-carrying insects of step b) are primarily leafcutter bees.

24. A method for the efficient production of seeds capable of growing male fertile $F_1$ hybrid *Glycine max* plants according to claim 19, wherein said herbicide resistance gene is resistant to a herbicide selected from the group consisting of glyphosate, sulfonylurea, glufosinate, isoxaflutole or protoporphyrinogen oxidase inhibitors.

25. The method of claim 19, wherein seed of said male sterile female parent line is planted in separate rows in the field from said male fertile soybean variety.

26. The method of claim 19, wherein seed set on said male sterile plants is greater than 30%.

27. A method to create a blend of hybrid and variety seed comprising:
   a) planting seed of a male sterile female parent line, having a male sterile gene linked to a herbicide resistance gene, adjacent to seed of a male fertile male soybean variety;
   b) allowing male sterile female soybean plants to cross-pollinate with male fertile soybean plants with the aid of pollen-carrying insects; and
   c) harvesting a blend of hybrid and selfed soybean seed.

28. The method of claim 27, wherein said blend of hybrid and selfed soybean seed is screened to decrease a percentage of smaller variety seed versus larger hybrid seed.

29. The method of claim 27, wherein seed set on said male sterile plants is greater than 30%.

* * * * *